(12) United States Patent
Taylor

(10) Patent No.: US 8,075,367 B2
(45) Date of Patent: Dec. 13, 2011

(54) ABSORBENT PAD FOR UNDERWIRE BRASSIERE

(76) Inventor: Candis A. Taylor, Plano, TX (US)

( * ) Notice: Subject to any disclaimer, the term of this patent is extended or adjusted under 35 U.S.C. 154(b) by 167 days.

(21) Appl. No.: 12/458,697

(22) Filed: Jul. 21, 2009

(65) Prior Publication Data
US 2010/0022164 A1    Jan. 28, 2010

Related U.S. Application Data

(60) Provisional application No. 61/129,850, filed on Jul. 24, 2008.

(51) Int. Cl.
 *A41C 3/00* (2006.01)
(52) U.S. Cl. ............... 450/37; 2/53; 2/56; 2/57
(58) Field of Classification Search ........... 450/36–38, 450/54–57, 92, 93; 2/73, 267, 268, 53, 56, 2/57, 1, 455, 463
See application file for complete search history.

(56) References Cited

U.S. PATENT DOCUMENTS

| | | | | |
|---|---|---|---|---|
| 1,026,326 | A | * | 5/1912 | LePorin ................ 450/56 |
| 2,633,440 | A | * | 3/1953 | Scholl .................. 428/40.1 |
| 5,217,782 | A | | 6/1993 | Moretz et al. |
| 5,603,653 | A | | 2/1997 | Hartman |
| 5,664,984 | A | * | 9/1997 | Laughridge ............. 450/57 |
| 5,716,255 | A | * | 2/1998 | Abercrombie et al. ...... 450/60 |
| 5,980,359 | A | * | 11/1999 | Brown ................... 450/57 |
| 6,203,399 | B1 | | 3/2001 | Hackney |
| 6,264,530 | B1 | | 7/2001 | Cosentino |
| 6,341,377 | B1 | | 1/2002 | Faries, Jr. et al. |
| 6,406,353 | B1 | | 6/2002 | Harper |
| D554,326 | S | | 11/2007 | Nuse |
| 7,905,763 | B1 | * | 3/2011 | Frank ................... 450/37 |
| 2007/0099542 | A1 | * | 5/2007 | Sakaguchi et al. ......... 450/37 |

FOREIGN PATENT DOCUMENTS

JP        9296308        11/1997

* cited by examiner

*Primary Examiner* — Gloria Hale
(74) *Attorney, Agent, or Firm* — Richard C. Litman

(57) ABSTRACT

The absorbent pad for an underwire brassiere includes a sealed cover layer having opposed first and second surfaces and defining an open interior region therein. The first surface is porous, allowing for passage of perspiration into the open interior region. An absorbent layer is positioned within the open interior region of the sealed cover layer, and the absorbent layer is formed from a hydrophilic material. An adhesive layer is formed on the second surface of the sealed cover layer, so that the adhesive layer releasably adheres the absorbent pad to a lower edge of one cup of the underwire brassiere. The absorbent pad is dimensioned and configured to completely cover an underwire of the cup so that the absorbent pad absorbs perspiration of the wearer and provides protective padding over the underwire.

19 Claims, 3 Drawing Sheets

ABSORBENT PAD FOR UNDERWIRE BRASSIERE

CROSS-REFERENCE TO RELATED APPLICATION

This application claims the benefit of U.S. Provisional Patent Application Ser. No. 61/129,850, filed Jul. 24, 2008.

BACKGROUND OF THE INVENTION

1. Field of the Invention

The present invention relates to undergarments, and particularly to absorbent pads for an underwire brassiere that absorbs perspiration and also provides padded coverage of the underwires.

2. Description of the Related Art

The additional warmth and coverage provided by a brassiere often causes women to perspire at a greater rate in the areas covered by the brassiere, particularly in the regions about the bases of the breasts. Numerous methods have been employed in order to eliminate or lessen the moisture and odor caused by perspiration. Such methods include dress shields, the use of deodorizing sprays, perfumes and powders, such as talc. Although perfumes work well to combat perspiration odor, they are only effective for a short period of time. In addition, such measures do not alleviate the chafing and other physical discomfort that may be caused by the collection of perspiration beneath the breasts, which may cause rashes or other skin irritation. A disadvantage of powders, such as talc, is that they cake and flake after becoming moist, and may filter through the user's blouse or dress material, thus causing discoloration of the clothing.

In addition to the problems associated with perspiration, underwire brassieres can be uncomfortable for the wearer, as the wire is typically stiff and may poke or abrade the wearer. Thus, an absorbent pad for an underwire brassiere solving the aforementioned problems is desired.

SUMMARY OF THE INVENTION

The absorbent pad for an underwire brassiere provides absorption of perspiration to keep the skin dry, particularly under the breast, as well as padded coverage of the underwire. The absorbent pad for an underwire brassiere includes a sealed cover layer having opposed first and second surfaces and defining an open interior region therein. The first surface is porous, allowing for the passage of perspiration into the open interior region.

An absorbent layer is positioned within the open interior region of the sealed cover layer, with the absorbent layer being formed from a hydrophilic material for absorbing the perspiration. In addition, the interior region may contain an antibacterial layer, formed from an antibacterial material.

An adhesive layer is formed on the second surface of the sealed cover layer, so that the adhesive layer releasably adheres the absorbent pad to a lower edge of one cup of the underwire brassiere. The absorbent pad is dimensioned and configured to completely cover an underwire of the cup, so that the absorbent pad absorbs perspiration of the wearer and provides protective padding for the wearer from the underwire.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
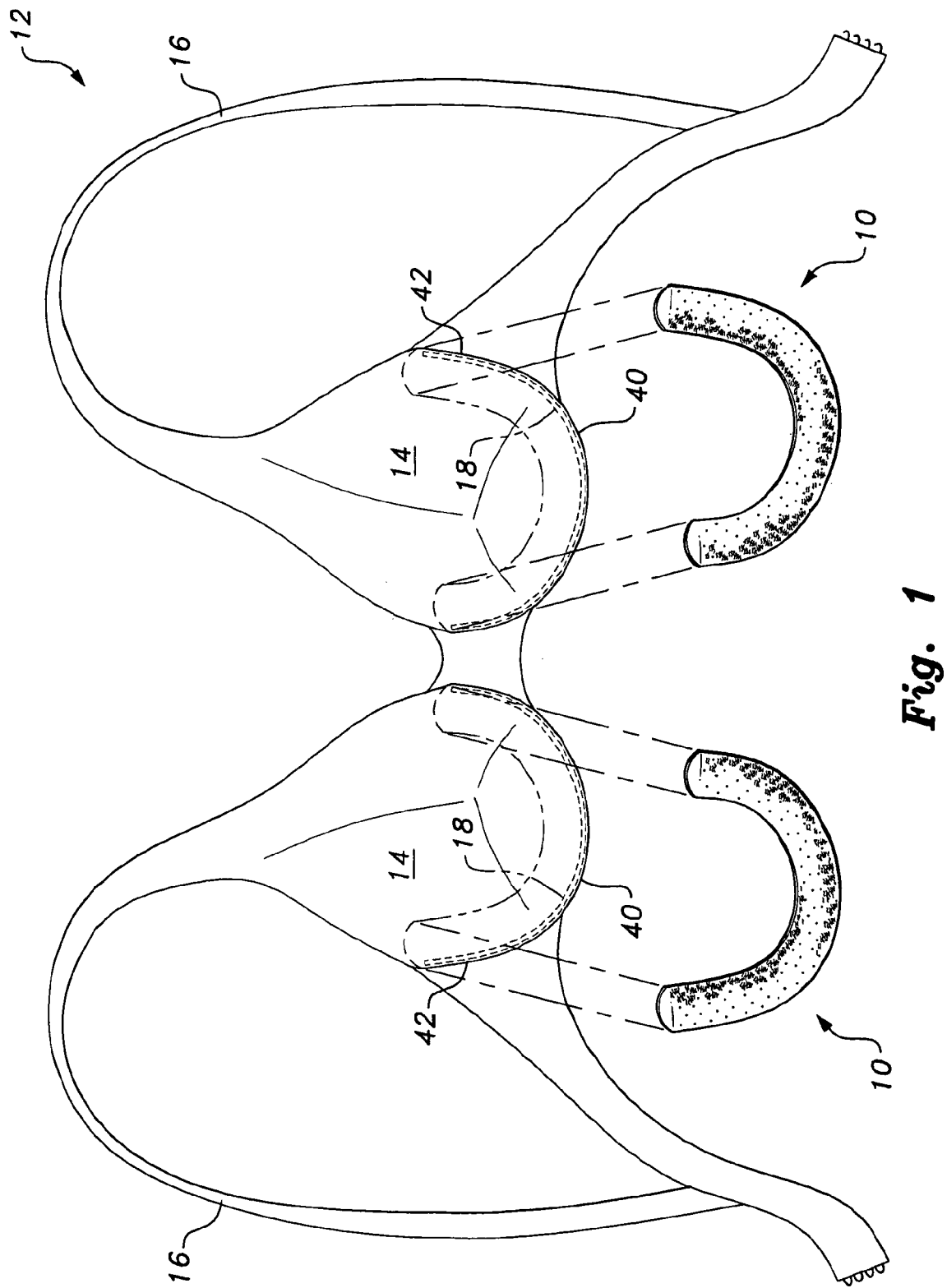
FIG. 1 is an exploded perspective view of a pair of absorbent pads for an underwire brassiere according to the present invention.

The present invention is directed towards an absorbent pad for an underwire brassiere, designated generally as 10 in the drawings. A pair of the absorbent pads 10 are shown in FIG. 1. The pads 10 provide absorption of perspiration that sometimes accumulates under the breasts, as well as padded coverage of the underwires 18. Brassiere 12, shown for exemplary purposes only, is a conventional underwire brassiere, having a pair of cups 14 and a pair of straps 16. Each cup 14 has an underwire 18 built into the cup 14 and positioned against a lower edge 40 thereof. As shown, the underwire 18 extends at least partially up an outer side edge 42 of the respective cup 14. Each absorbent pad 10 is dimensioned and configured to completely cover the respective underwire 18. Further, it should be understood that absorbent pads 10 may be manufactured in a variety of dimensions and configurations in order to match a variety of sizes and shapes of respective brassieres.

Figure 2:
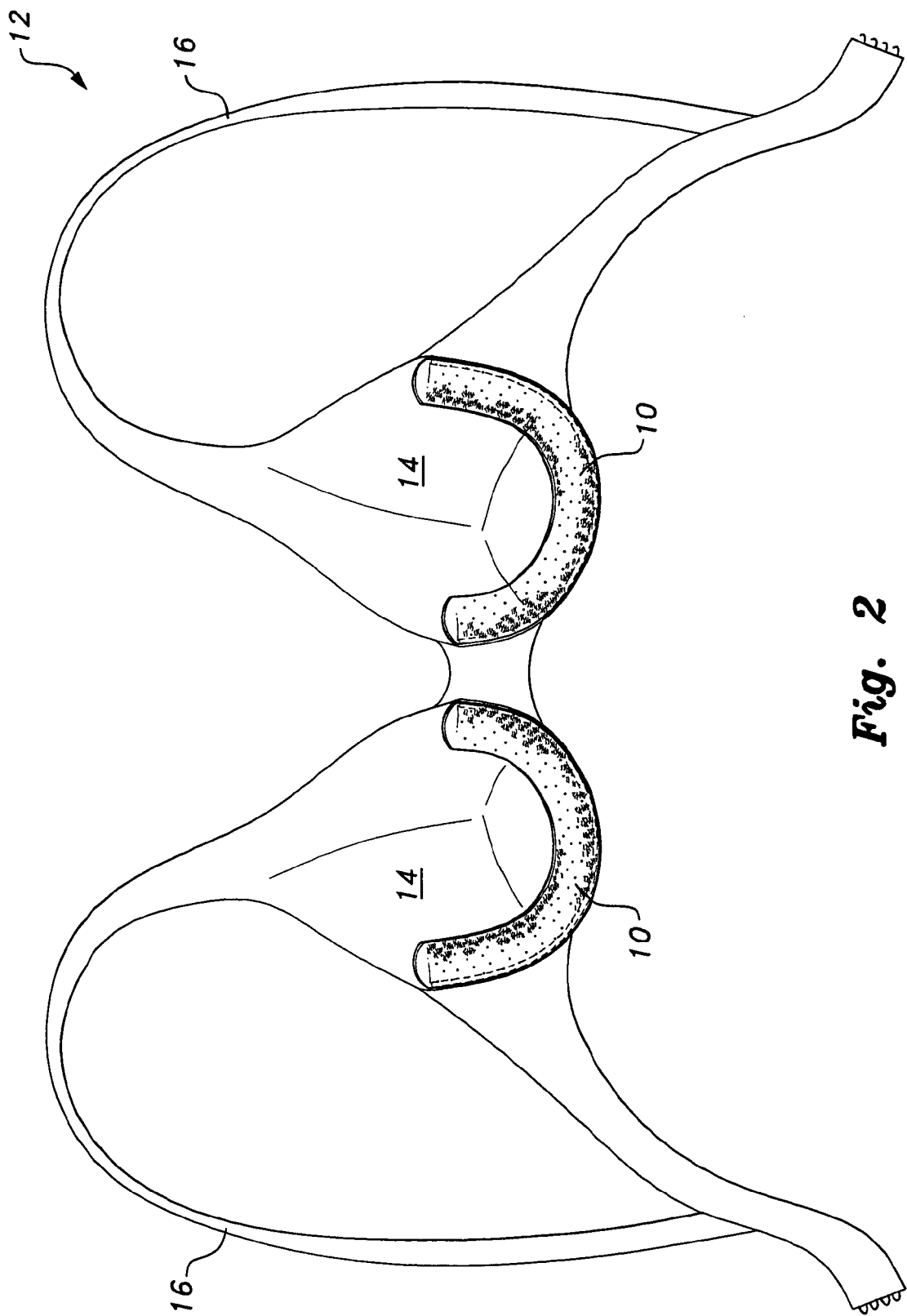
FIG. 2 is a perspective view of a brassiere having the absorbent pads for an underwire brassiere according to the present invention attached thereto.
Figure 3:
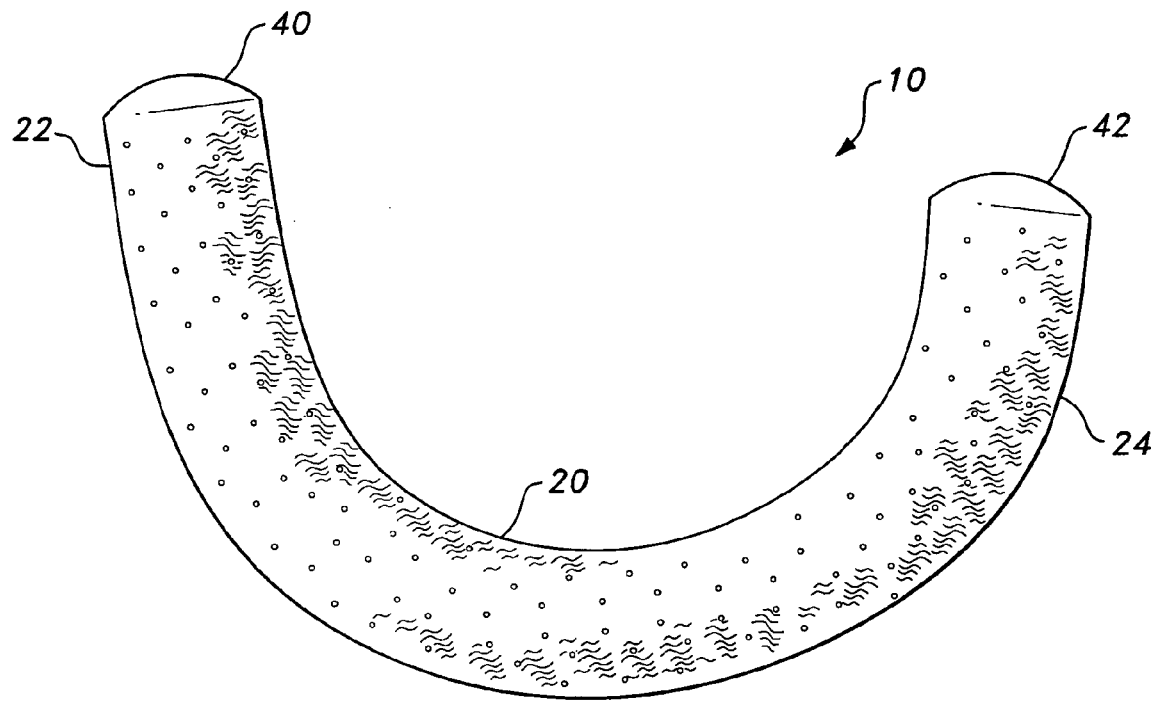
FIG. 3 is a front view of the absorbent pad for an under wire brassiere according to the present invention.

As best shown in FIG. 3, each absorbent pad 10 has a substantially arcuate contour, which may generally be described as J-shaped, in order to conform to the curvature of the breast, with the longer leg of the arc being positioned laterally and the shorter leg of the being positioned medially. The absorbent pad 10 shown in FIG. 3 is an absorbent pad adapted for attachment to the leftmost cup 14 in FIGS. 1 and 2, an absorbent pad for the right side being a mirror image thereof. In FIG. 3, the lateral end 22 of pad 10 is positioned above central portion 20 and the opposed medial end 24. This configuration matches the contour of underwire 18 of the leftmost cup 14 of the brassiere 12 shown in FIGS. 1 and 2. The rightmost pad 10 of FIGS. 1 and 2 is formed symmetrically about the central, vertical axis of the brassiere 12 to match the contour of the respective underwire 18 of the rightmost cup 14. Pads 10, in addition to providing absorption of perspiration, provide padding for the user against abrasion by the underwires 18. Thus, the ends 22 of pads 10 are configured to extend up side edges 42 of each cup 14 in order to cover the respective underwires 18. It should be noted that the top surfaces 40, 42 of ends 22, 24, respectively, are preferably rounded so as to be comfortable and non-abrasive when pressed against the user's skin.

Figure 4:
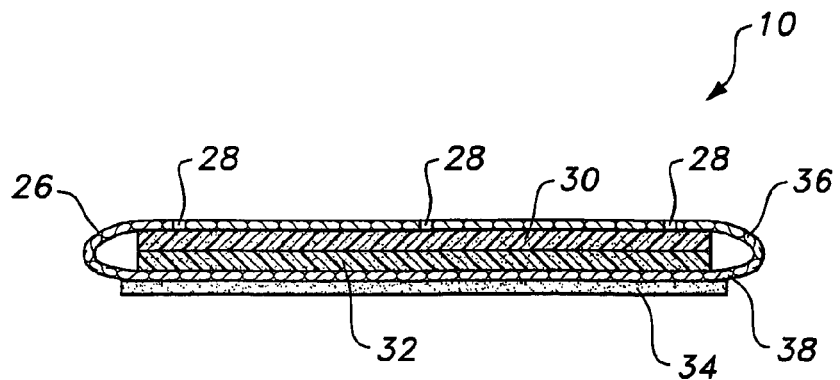
FIG. 4 is a transverse view in section of an absorbent pad for an underwire brassiere according to the present invention.

As best shown in FIG. 4, each absorbent pad 10 includes a sealed cover layer 26 having opposed first and second surfaces 36, 38, respectively, that define an open interior region therein. The first surface 36 is porous, having a plurality of openings 28 formed therethrough that allow for the passage of perspiration into the open interior region. Cover layer 26 may be formed from any suitable fabric material, such as cotton, rayon, polyester, or other soft natural or synthetic fibers.

An absorbent layer 30 is positioned within the open interior region of the sealed cover layer 26, with the absorbent layer 30 being formed from a hydrophilic material, or having a hydrophilic material embedded or intermixed therein, for absorbing the perspiration of the wearer. Any suitable hydrophilic material, such as baking soda, may be used. Additionally, an antibacterial layer 32, formed from any suitable antibacterial material, may also be contained within the open interior region of the sealed cover layer 26. Antibacterial layer 32 prevents the generation and proliferation of bacteria in the warm and damp environment of the interior of the pad, and also reduces the odors emitted by the wearer's perspiration.

An adhesive layer 34 is formed on the second surface 38 of the sealed cover layer 26, so that the adhesive layer 34 releasably and removably adheres the absorbent pad 10 to the lower edge 40 of one cup 14 of the underwire brassiere 12. Each absorbent pad 10 is dimensioned and configured to cover the underwire 18 of the respective bra cup 14 so that the absorbent pad 10 absorbs perspiration of the wearer and provides protective padding for the wearer from the underwire 18. Each absorbent pad 10 may be provided with a release layer, as is conventionally known, for covering the adhesive layer 34 until time of use thereof.

It is to be understood that the present invention is not limited to the embodiment described above, but encompasses any and all embodiments within the scope of the following claims.

I claim:

1. An absorbent pad for an underwire brassiere, comprising:
   a cover layer having opposed first and second surfaces and defining an open interior region therein, the first surface being porous, the cover layer being arcuate and having lateral and medial portions, the lateral arcuate portion extending upward from the medial portion and being longer than the medial portion, the cover layer being dimensioned and configured to overlay the underwire in a cup of the underwire brassiere;
   an absorbent layer contained within the open interior region defined by the cover layer, the absorbent layer being formed from a hydrophilic material; and
   an adhesive layer formed on the second surface of the cover layer.

2. The absorbent pad for an underwire brassiere as recited in claim 1, further comprising an antibacterial layer formed from an antibacterial material, the antibacterial layer being contained within the open interior region adjacent the absorbent layer.

3. The absorbent pad for an underwire brassiere as recited in claim 1, wherein said cover layer is substantially J-shaped.

4. The absorbent pad for an underwire brassiere as recited in claim 1, wherein opposed lateral and medial ends of said cover layer each have a rounded contour.

5. The absorbent pad for an underwire brassiere as recited in claim 2, wherein said absorbent layer is positioned adjacent and contiguous to the first surface of said cover layer.

6. The absorbent pad for an underwire brassiere as recited in claim 5, wherein the antibacterial layer is positioned adjacent the absorbent layer and contiguous to the second surface of said cover layer.

7. An underwire brassiere with removable absorbent pads, comprising:
   an underwire brassiere having a pair of cups defining a lower edge and an underwire supporting each cup along the lower edge thereof, each of the cups having a lateral curvature and a medial curvature;
   a pair of absorbent pads, each of the pads having:
      a cover layer having opposed first and second surfaces defining an open interior region therebetween, the first surface being porous;
      an absorbent layer contained within the open interior region defined by the cover layer, the absorbent layer being formed from a hydrophilic material; and
      an adhesive layer disposed on the second surface of the cover layer, the adhesive layer removably attaching the absorbent pads to the bra cups, the absorbent pads overlaying the underwires in the bra cups.

8. The underwire brassiere with removable absorbent pads as recited in claim 7, wherein each said absorbent pad further comprises an antibacterial layer formed from an antibacterial material, the antibacterial layer being contained within the open interior region adjacent the absorbent layer.

9. The underwire brassiere with removable absorbent pads as recited in claim 7, wherein each said absorbent pad is substantially J-shaped.

10. The underwire brassiere with removable absorbent pads as recited in claim 7, wherein opposed lateral and medial ends of said cover layer of each said absorbent pad each have a rounded contour.

11. The underwire brassiere with removable absorbent pads as recited in claim 8, wherein said absorbent layer of each said absorbent pad is positioned adjacent and contiguous to the first surface of said cover layer.

12. The underwire brassiere with removable absorbent pads as recited in claim 11, wherein the antibacterial layer of each said absorbent pad is positioned adjacent said absorbent layer and contiguous to the second surface of said cover layer.

13. An underwire brassiere with removable absorbent pads, comprising:
   an underwire brassiere having a pair of cups defining a lower edge and an underwire supporting each cup along the lower edge thereof, each of the cups having a lateral curvature and a medial curvature;
   a pair of absorbent pads, each of the pads having:
      a cover layer having opposed first and second surfaces defining an open interior region therebetween, the first surface being porous;
      an absorbent layer contained within the open interior region defined by the cover layer, the absorbent layer being formed from a hydrophilic material; and
      means for removably attaching the absorbent pads to the bra cups, the absorbent pads overlaying the underwires in the bra cups.

14. The underwire brassiere with removable absorbent pads as recited in claim 13, wherein each said absorbent pad further comprises an antibacterial layer formed from an antibacterial material, the antibacterial layer being contained within the open interior region adjacent the absorbent layer.

15. The underwire brassiere with removable absorbent pads as recited in claim 13, wherein each said absorbent pad is substantially J-shaped.

16. The underwire brassiere with removable absorbent pads as recited in claim 13, wherein opposed lateral and medial ends of said cover layer of each said absorbent pad each have a rounded contour.

17. The underwire brassiere with removable absorbent pads as recited in claim 16, wherein said absorbent layer of each said absorbent pad is positioned adjacent and contiguous to the first surface of said cover layer.

18. The underwire brassiere with removable absorbent pads as recited in claim 17, wherein the antibacterial layer of each said absorbent pad is positioned adjacent said absorbent layer and contiguous to the second surface of said cover layer.

19. The underwire brassiere with removable absorbent pads as recited in claim 13, wherein said means for removably attaching the absorbent pads to the bra cups comprise a pair of adhesive layers respectively disposed on the second surfaces of the cover layers of said absorbent pads.

* * * * *